United States Patent
Müller et al.

(10) Patent No.: US 8,202,540 B1
(45) Date of Patent: Jun. 19, 2012

(54) METHOD FOR CONTROLLED PRODUCTION OF ULTRAFINE MICROPARTICLES AND NANOPARTICLES

(75) Inventors: Rainer H. Müller, Berlin (DE); Karsten Krause, Berlin (DE); Karsten Mäder, Berlin (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 1120 days.

(21) Appl. No.: 10/030,417

(22) PCT Filed: Jul. 10, 2000

(86) PCT No.: PCT/EP00/06535
§ 371 (c)(1),
(2), (4) Date: Aug. 14, 2002

(87) PCT Pub. No.: WO01/03670
PCT Pub. Date: Jan. 18, 2001

(30) Foreign Application Priority Data

Jul. 13, 1999 (DE) .................................. 199 32 157

(51) Int. Cl.
*A61K 9/10* (2006.01)
*A61K 9/14* (2006.01)
*A61K 9/51* (2006.01)

(52) U.S. Cl. ........ 424/489; 424/497; 424/487; 424/114; 424/494; 424/499

(58) Field of Classification Search .................. 428/489
See application file for complete search history.

(56) References Cited

U.S. PATENT DOCUMENTS

| | | | |
|---|---|---|---|
| 5,091,187 A | | 2/1992 | Haynes |
| 5,104,674 A | * | 4/1992 | Chen et al. ..................... 426/573 |
| 5,510,118 A | | 4/1996 | Bosch et al. |
| 5,858,410 A | * | 1/1999 | Muller et al. ................. 424/489 |

FOREIGN PATENT DOCUMENTS

| | | |
|---|---|---|
| DE | 44 40 337 A1 | 5/1996 |
| EP | 0 778 083 A1 | 6/1997 |
| WO | WO 9814174 * | 4/1998 |
| WO | WO 9814174 A1 * | 4/1998 |
| WO | WO 99/61001 A1 | 12/1999 |
| WO | WO 00/25772 A1 | 5/2000 |

OTHER PUBLICATIONS

Brown, Theodore. LeMay, Eugen. Bursten, Bruce. Chemistry, The Central Science. 1994 New Jersey: Prentice-Hall, Inc. pp. 476, and 477.*

* cited by examiner

*Primary Examiner* — Michael G Hartley
*Assistant Examiner* — Nabila Ebrahim
(74) *Attorney, Agent, or Firm* — Jeffrey S. Melcher; Manelli Selter PLLC (57) ABSTRACT

The invention relates to superfine microparticles and nanoparticles and a process for their gentle preparation with exclusion of water or minimization of water and/or exclusion of plasticizers and/or reduced temperature load, in which a matrix material is subjected to a high-pressure homogenization process in an anhydrous or water-poor medium and/or at low temperatures, preferably room temperature (20° C.) and in particular below the freezing point of water, which leads to a gentle particle reduction with minimization of the impairment of the chemical stability of the homogenized material.

36 Claims, 4 Drawing Sheets

METHOD FOR CONTROLLED PRODUCTION OF ULTRAFINE MICROPARTICLES AND NANOPARTICLES

CROSS-REFERENCE TO RELATED APPLICATIONS

This application is a national stage entry under 35 U.S.C. 371 of International Application No. PCT/EP00/06535, filed 10 Jul. 2000, designating the United States. This application claims foreign priority under 35 U.S.C. 119 and 365 to Danish Patent Application No. 19932157.4, filed 13 Jul. 1999.

The invention relates to superfine microparticles and nanoparticles and a process for their gentle preparation with exclusion of water or minimization of water and/or exclusion of plasticizers and/or reduced temperature load.

BACKGROUND TO THE INVENTION

Micro- and nanoparticles can be divided into three large groups according to their composition, namely particles composed of:
I. pure drug,
II. pure matrix material (e.g. polymers, natural macromolecules, lipids),
III. matrix material loaded with active ingredient.

Particle sizes over 10 μm are easily accessible by conventional size reduction techniques, e.g. grinding with a pestle, optionally accompanied by nitrogen cooling. It is more difficult to prepare superfine particles smaller than 10-20 μm and in particular nanoparticles smaller than 1 μm, in particular in the range of a few 100 nm.

Air-jet milling gives particle distributions of up to 25 μm (Peters, K., Nanosuspensions for the i.v. administration of poorly soluble drugs—stability during sterilization and long-term storage, $22^{nd}$ Int. Symp. CRS, 1995, 2212); in addition, the thermal load and exposure to oxygen can impair the chemical stability of sensitive active ingredients.

Although wet-grinding processes (List, P. H., Arzneiformenlehre, $3^{rd}$ Edition, 1982, WVG, Stuttgart) in water reduce the temperature load upon suitable cooling, they are unsuitable for hydrolysis-sensitive active ingredients.

An alternative preparation process is the precipitation of the particles, e.g. for the preparation of drug nanoparticles (so-called hydrosols) (Sucker, H., Hydrosole-eine Alternative far die parenterale Anwendung von schwer wasserlöslichen Wirkstoffen, in: Müller, R. H., Hildebrand, G. E., (Eds.), Pharmazeutische Technologie: Moderne Arzneiformen, $2^{nd}$ Edition, 1998, WVG, Stuttgart). A disadvantage here is that organic solvents must be used as a rule (residue in the product). A further problem is that the drug must at least be soluble in a solvent. At the same time, this solvent must also be miscible with a non-solvent in order to precipitate out the particles by the addition of the solvent to the non-solvent according to Ostwald-Mier. The resulting particles must then be prevented from growing during the precipitation process by skilful selection of the stabilizing surfactant mixture and be stabilized for long-term storage.

Other processes for preparing micro- and nanoparticles are e.g. spray-drying (Wagenaar, B. W., Müller, B. W., Piroxicam release from spray-dried biodegradable microspheres, Biomaterials 1994, 15, 49-53), solvent evaporation methods (Nihant, N., et al, Polylactide Microparticles Prepared by Double Emulsion/Evaporation Technique. I. Effect of Primary Emulsion Stability, Pharm. Res., 1994, 11, 1479-1484), solvent deposition and phase separation (Speiser, P. P., Nanopartikel, in: Müller, R. H., Hildebrand, G. E., (Eds.), Pharmazeutische Technologie: Moderne Arzneiformen, $2^{nd}$ edition, 1998, WVG, Stuttgart, 339-357). However, all contain organic solvents as a rule, and in addition, contact with water is unavoidable (Fahr, A. Kissel, T., Mikropartikel and Implantate: Arzneiformen zur parenteralen Applikation, in: Müller, R. H., Hildebrand, G. E., (Eds.), Pharmazeutische Technologie Moderne Arzneiformen, $2^{nd}$ Edition, 1998, WVG, Stuttgart, 243-259).

As an alternative process for preparing micro- and nanoparticles via particle reduction whilst avoiding organic, toxicologically problematical solvents, high-pressure homogenization was then used. The polymer to be reduced (Müller, B. W., Verfahren zur Herstellung von Pseudolatices und Mikro- oder Nanopartikeln und diese enthaltenden pharmazeutischen Prdparaten, EP 0 605 933 B1, 1998) or drug (Liversidge, G. G. Surface-modified drug nanoparticles, U.S. Pat. No. 5,145,684, 1991; Haynes, D. H., Phospholipid-coated microcrystals: injectable formulations of water-insoluble drugs, U.S. Pat. No. 5,091,187, 1992; Westesen, K., Solid lipid particles, particles of bioactive agents and methods for the manufacture and use thereof, International Patent Application WO 94/20072, 1994) is dispersed in water and the suspension then passed through the high-pressure homogenizer. A disadvantage here is that in the case of all processes, the particles to be reduced are exposed to water. In particular, it is stated that, in the case of polymers, the temperature load is also to be raised and possibly a toxicologically undesirable plasticizer must be added, e.g. 0.3-10% in the case of ethyl cellulose (Müller, B. W., Verfahren zur Herstellung von Pseudolatices und Mikro-oder Nanopartikeln und diese enthaltenden pharmazeutischen Präparaten, EP 0 605 933 B1, 1998). Drugs are also melted (Westesen, K., Solid lipid particles, particles of bioactive agents and methods for the manufacture and use thereof, International Patent Application WO 94/20072, 1994) which, in addition to the impairment of chemical stability, also tend not to crystallize again after homogenization (Siekmann, B., Westesen, K., Preparation and physicochemical characterization of aqueous dispersions of coenzyme Q10 nanoparticles, Pharm. Res., 1995, 12, 201-208).

Thus in general, for a gentler size reduction process, depending on the properties of the material to be homogenized, it is necessary:
to minimize or exclude contact with water
to exclude the use of toxicologically undesirable organic solvents such as dichloromethane
to minimize or avoid the temperature load
to avoid the addition of toxicologically undesirable additives such as plasticizers
to minimize or exclude exposure to oxygen
to avoid melting and to keep the substances to be processed in solid state.

The present invention realizes a gentle reduction process by homogenization in which, depending on the properties of the substance to be processed, one or more or all of these parameters are fulfilled simultaneously. If the meeting of a parameter is not essential (e.g. exclusion of oxygen is not necessary), then it waived avoided on economic grounds in order to make the process as economical as possible.

The reduction principle of high-pressure homogenization is cavitation (Müller, R. H., Böhm, B. H. L., Grau, M. J., Nanosuspensions—Formulierungen für schwerlösliche Arzneistoffe mit Beringer Bioverfügbarkeit: I. Herstellung and Eigenschaften, Pharm. Ind., 1999, 74-78). Water boils when the static pressure acting on it (e.g. air pressure) is equal to or less than the vapour pressure. In the high-pressure homogenizer, liquid flows at a very high speed so that the static pressure sinks below the vapour pressure of water, this is transformed into the gaseous state and forms gas bubbles. When the gas bubbles collapse (e.g. on leaving the homogenization gap), this implosion leads to strong shock waves which lead to particle reduction. The reduction of substances by high-pressure homogenization was therefore previously carried out in water and not in liquids with a lower vapour pressure. Even high-pressure homogenization at increased temperature is recommended load (well above room temperature, e.g. at 60-90° C.) as the difference between static pressure (e.g. in homogenization gap) and vapour pressure of the water can then be more easily overcome. In particular, homogenization was not carried out at lower temperatures as, because the vapour pressure of the water is less at lower temperatures, the difference between static pressure and vapour pressure increases and no cavitation occurs. In particular when reducing polymers, even a temperature increase is described as insufficient for an effective reduction, and plasticizers must be added to the polymers (Müller, B. W., Verfahren zur Herstellung von Pseudolatices und Mikro-oder Nanopartikeln und diese enthaltenden pharmazeutischen Präparaten, EP 0 605 933 B1, 1998).

In the invention, it is not water but non-aqueous liquids, in particular also with a lower vapour pressure (liquid polyethylene glycols, anhydrous glycerine) that are used in the homogenization process. Surprisingly, it was shown that superfine microparticles and nanoparticles could also be prepared thereby (examples 1-6). Compared with particles which were homogenized in water, negligible differences resulted (example 3). Homogenization in anhydrous media was carried out for pure active ingredients (e.g. drugs, cosmetic active ingredients, etc.), synthetic polymers and natural macromolecules as well as for active-ingredient-charged polymers.

Depending on the degree of hydrolysis sensitivity of active ingredients, small proportions of water are tolerated in the dispersion medium. Thus proportions of water were added to the dispersion medium in order to improve the uniformity of the particle dispersion (example 7). The average diameter of the particle dispersion shows little change compared with anhydrous dispersion medium (example 6). However, the 95% diameter sinks slightly, which is an indication of the presence of a few larger particles in addition to the main population of the particles (example 13). Irrespective of this, certain proportions of water are often desired in the further processing of the particle dispersion (e.g. in PEG 400 upon packing in soft gelatine capsules, the PEG should contain a certain proportion of moisturiser so that no water is removed from the gelatine capsule wall itself and the capsule thereby becomes brittle). A condition for this is however at least a low solubility of water in the dispersion medium or miscibility. Added water proportions were e.g. 1%, 5% and 10% (e.g. example 7). Surprisingly, these water proportions—contrary to the theoretical considerations—had no reduction-promoting influence (little change in 50% diameter).

Higher proportions of water were also used (the maximum quantities of water used were 80% or 99%), the particle size decreasing insubstantially or not at all compared with the anhydrous medium (e.g. examples 7 and 8). For most products, such minimal differences are irrelevant to product quality. For suspensions for intravenous injection, it is irrelevant to the avoidance of capillary blockage whether the average diameter is 0.6 µm or 0.7 µm as long as it remains clearly below the smallest size of capillaries of 5-6 µm for the avoidance of capillary blockage (embolism). These results confirm that an external water phase is not necessary to achieve a product of sufficient fineness.

The proportion of microparticles with a size clearly above the average 50% diameter is a function of the number of homogenization cycles. It decreases (i.e. the D95% or D90% as a measure of this proportion decreases) as the number of cycles increases (example 13). To reduce the proportion of microparticles—e.g. in view of i.v. application—the number of cycles can generally be increased so that an addition of water to the dispersion medium is not necessary for this either.

An addition of water which does not impair the stability of active ingredients is also advisable if substances or polymers are dissolved in this water which are not, or not sufficiently, soluble in the anhydrous solvent, but are desirable for the final formulation. Examples are hydroxypropyl methylcellulose (HPMC) as a structuring excipient or PEG 6000 as mould release agent if the micro- or nanoparticle dispersion is to be converted into a dry formulation such as a tablet or pellet. Gelation agents, e.g. miglyol gel (solution of Aerosil with low water content to promote gelation in oil via hydroxyl groups of the water) are also advisable.

To examine the influence of a plasticizer, in a comparable manner to Müller, B. W., Verfahren zur Herstellung von Pseudolatices und Mikro-oder Nanopartikeln und diese enthaltenden pharmazeutischen Präparaten, EP 0 605 933 B1, 1998, ethyl cellulose with an added 1.74% (m/m relative to the polymer) plasticizer was homogenized at increased temperature and compared with a microparticle suspension prepared without added plasticizer (example 9). The differences in the particle sizes were small or the plasticizer-free dispersion surprisingly even showed smaller particle sizes, so that toxicologically undesired plasticizers can be dispensed with—contrary to expectations on the basis of the literature.

For polymers such as ethyl cellulose (Müller, B. W., Verfahren zur Herstellung von Pseudolatices und Mikro-oder Nanopartikeln und diese enthaltenden pharmazeutischen Präparaten, EP 0 605 933 B1, 1998), homogenization at higher temperatures should lead to smaller particles. This is based on the theoretical considerations that the difference between static pressure in the homogenizer and the vapour pressure of the dispersion medium is smaller and the softening point of the polymers is approached. Ethyl cellulose was therefore homogenized at different temperatures and the particle sizes compared (example 10). The differences were minimal and as a rule not relevant for the product quality. Thus operation is also possible for these substances at 40-60° C. or slightly above or at room temperature (20° C.) instead of 85° C. without loss of product-relevant quality or particle size.

High-pressure homogenization involves the dissipation of flow energy in heat (Jahnke, S., Theorie der Hochdruckhomogenisation, Workshop Dispergiertechnik, 4$^{th}$ Expert Meeting, cdc 1999), the product warms up (e.g. per cycle by approx. 10-20° C. in the case of LAB 40, APV Deutschland GmbH, Lubeck, Germany). For very temperature-sensitive substances, removal of this heat from the product should not wait until the product container stage but preferably already take place beforehand in the homogenization tower during the reduction process. In these cases, the process is carried out at lower temperature (example 14), i.e. with cooling at 4° C. or else well below 0° C., e.g. at −20° C. or −50° C., which is only possible as a purely external phase avoiding water. Contrary to theoretical considerations (even lower vapour pressure of water at these low temperatures), the high pressure homogenization was, surprisingly, sufficiently effective for preparing superfine particle dispersions. Further measures are degassing of the dispersion medium (e.g. in a vacuum or by heating) and additionally protective gassing (e.g. with nitrogen) (example 16).

DETAILED DESCRIPTION OF THE INVENTION

The substance to be converted into superfine microparticles or nanoparticles (e.g. active ingredients, polymers or active-ingredient-loaded polymers) is dispersed as powder accompanied by stirring in a liquid medium (dispersion medium) to prepare a pre-suspension. Dispersion can be carried out with mixers of various designs, e.g. propeller mixer, rotor-stator mixer (Ultra-Turrax), dissolver discs. Alternatively, the powdered substance can also be gradually wetted, e.g. with a mortar (mortar mill). Dispersion medium is progressively added to the substance in the mortar during mixing.

All liquids apart from water with sufficiently low viscosity can be used as dispersion media, e.g.

polyols such as e.g. glycerine, polyethylene glycols (PEGs) (e.g. PEG 400 and PEG 600), polyether and polyester polyols, glycols such as e.g. propylene glycol, ethylene glycol, oils such as e.g. medium chain triglycerides (MCT) (e.g. miglyols), long chain triglycerides (LCT) such as e.g. isopropyl myristate, vegetable oils such as avocado oil, cottonseed oil, safflower oil, peanut oil, jojoba oil, coconut oil, linseed oil, walnut oil, olive oil, palm-kernel oil, sesame oil, soybean oil, castor oil, wheat-germ oil, animal oils such as cod-liver oil, halibut-liver oil, neat's foot oil, liquid hydrocarbons such as e.g. liquid paraffin, viscous paraffin and hexane, alcohols such as methanol, ethanol, 1-propanol, isopropanol, n-butanol, 2-butanol, pentanol, hexanol, octanol, decanol, allyl alcohol, propargyl alcohol.

If desirable for the final product, a proportion of water can be added to the dispersion medium (e.g. addition of water to PEG 400 with a view to a later packing in soft gelatine capsules). As a rule, the water proportions lie in the range from 1 to 10%, but higher proportions can also be used. A limiting factor in this case is the chemical stability of the substance to be homogenized. Although higher proportions of water have no or little effect on the average diameter of the prepared particle dispersion, the proportion of larger particles is additionally minimized. As a rule, the 95% diameter decreases slightly. For many products, this is of no relevance. It is useful however in the preparation of nanoparticle dispersions for intravenous injection. If too many particles larger than 5 μm remain in the product, this can lead to capillary blockage.

Substances such as HPMC, PEG 6000 or Aerosil can also be dissolved in the water if this is desirable for the sought final formulation to which the micro- and nanoparticle dispersions are to be processed. These are important in particular with regard to the manufacture of tablets, e.g. calcium phosphates, lactose, starch and its derivates such as starch hydrolysates, celluloses, cellulose derivatives, polyethylene glycols, polyvinylpyrrolidone (PVP), hexites, glucose; with regard to the manufacture of ointments, substances such as bentonite, Aerosil, cellulose ethers, cellulose esters, alginates, pectinates, tragacanth, polyvinyl alcohol, polyethylene glycols, gum arabic, polyacrylates, paraffin, polymethacrylates, petrolatum, plastibases, can be considered; and with regard to the processing into capsules, e.g. polyethylene glycols, paraffin, liquid triglycerides (vegetable or animal) are important.

To stabilize the suspension and the micro- and nanoparticles prepared from it, stabilizing substances can be added to the dispersion medium. Examples of this are:

1. sterically stabilizing substances such as poloxamers and poloxamines (polyoxyethylene-polyoxypropylene block copolymers), ethoxylated sorbitan fatty acid esters, in particular polysorbates (e.g. Polysorbate 80 or Tween 80®), ethoxylated mono- and diglycerides, ethoxylated lipids, ethoxylated fatty alcohols or fatty acids, and esters and ethers of sugars or of sugar alcohols with fatty acids or fatty alcohols (e.g. saccharose stearate, saccharose distearate, saccharose laurate, saccharose octanoate, saccharose palmitate, saccharose myristate).
2. charged ionic stabilizers such as diacetyl phosphates, phosphatidylglycerol, lecithins of various origins (e.g. egg lecithin or soybean lecithin), chemically modified lecithins (e.g. hydrogenated lecithins), as well as phospholipids and sphingolipids, mixture of lecithins with phospholipids, sterols (e.g. cholesterol and cholesterol derivatives as well as stigmasterol) and likewise charged and uncharged fatty acids, sodium cholate, sodium glycocholate, sodium taurocholate, sodium deoxycholate or their mixtures, amino acids or antiflocculants such as e.g. sodium citrate, sodium pyrophosphate, sodium sorbate [Lucks, J. S. et al. Int. J. Pharm., 1990, 58, 229-235]. Amphoteric-ionic surfactants such as e.g. (3-[(3-cholamidopropyl)-dimethylammonio]-2-hydroxy-1-propane sulfonate) [CHAPSO], (3-[(3-cholamidopropyl]-dimethylammonio]-1-propane sulfonate) [CHAPS] and N-dodecyl-N,N-dimethyl-3-ammonio-1-propane sulfonate. Cationic surfactants, in particular compounds used as preservatives, such as e.g. benzyldimethyl hexadecylammonium chloride, methylbenzethonium chloride, benzalkonium chloride, cetylpyridinium chloride.

The substances which can be used in the process for preparing superfine microparticles and nanoparticles are 1. pure substances (e.g. active ingredients in the pharmaceutical and cosmetic field)
2. polymers
3. active-ingredient-loaded polymers The pure substances are not restricted just to e.g. active ingredients in the pharmaceutical and cosmetic field but originate from very different fields (e.g. agronomics, foodstuffs). In the field of agriculture, a range of pesticides are unstable in water. They are therefore dissolved in the oil phase of an emulsion and this is prepared in highly concentrated form in order to minimize the water proportion. Nevertheless, stability in storage is limited. In the present process, chemically labile pesticides can be gently converted in an anhydrous process into fine nanoparticle dispersions which can then be applied to plants. In this case, homogenization in dispersion media miscible with water, e.g. PEG 400, is preferable. Before spraying, the nanoparticles dispersed in PEG are mixed with water and spraying is carried out with conventional spraying equipment.

In the field of foodstuffs, flavour enhancers for example, can be considered as active ingredients.

Furthermore, wood protection or polishing agents are of interest as active ingredients.

In the pharmaceutical field, principally active ingredients which have a too low bioavailability and/or are chemically unstable in water are of interest. A classic example is cyclosporin which has to date been on the market as a microemulsion (critical solution). The disadvantage of the microemulsion is the initially high plasma peak which is the reason for the nephrotoxicity. By conversion into a nanosuspension, the rate of solution is increased and thus the bioavailability compared with the powdered active ingredient, and the rapid diffusion of the active ingredient from a solution is simultaneously avoided. Another example is the HIV-effective substance azodicarbonamide (ADA). Conversion of ADA into nanoparticles using water as dispersion medium leads to a foamy dispersion. The microfoam formed remains stable over several weeks, the foamy product can thus not be further processed.

Drugs to be processed in this invention are e.g. from the therapeutic groups:

Analgesics/Antirheumatics
 BTM bases such as morphine, codeine, piritamide, fentanyl and fentanyl derivatives, levomethadone, tramadol, diclofenac, ibuprofen, indomethacin, naproxen, piroxicam, penicillamine Antiallergics
 pheniramine, dimethindene, terfenadine, astemizole, loratidine, doxylamine, meclozine, bamipine, clemastine Antibiotics/Chemotherapeutics
 of these: polypeptide antibiotics such as colistin, polymyxin B, teicoplanin, vancomycin; antimalarial products such as quinine, halofantrine, mefloquine, chloroquine, virostatics such as ganciclovir, foscarnet, zidovudine, acyclovir and others such as dapsone, fosfomycin, fusafungine, trimethoprim Antiepileptics
 phenyloin, mesuximide, ethosuximide, primidone, phenobarbital, valproic acid, carbamazepine, clonazepam Antimycotics
 a) internal:
  nystatin, natamycin, amphotericin B, flucytosine, miconazole, fluconazole, itraconazole
 b) in addition, external:
  clotrimazole, econazole, tioconazole, fenticonazole, bifonazole, oxiconazole, ketoconazole, isoconazole, tolnaftate Corticoids (Internal)
 aldosterone, fludrocortisone, betamethasone, dexamethasone, triamcinolone, fluocortolone, hydroxycortisone, prednisolone, prednylidene, cloprednol, methylprednisolone Dermatics
 a) antibiotics:
  tetracycline, erythromycin, neomycin, gentamycin, clindamycin, framycetin, tyrothricin, chlorotetracycline, mipirocin, fusidic acid
 b) virostatics as above, in addition:
  podophyllotoxin, vidarabine, tromantadine
 c) corticoids as above, in addition:
  amcinonide, fluprednidene, alclometasone, clobetasol, diflorasone, halcinonide, fluocinolone, clocortolone, flumethasone, diflucortolone, fludroxycortide, halomethasone, desoximethasone, fluocinolide, fluocortinbutyl, prednicarbate, desonide Diagnostics
 a) radioactive isotopes such as Te99m, In111 or I131, covalently bound to lipids or lipoids or other molecules or in complexes
 b) highly-substituted iodine-containing compounds such as e.g. lipids Haemostiptics/Anti-Hemorrhagics
 blood-coagulation factors VIII, IX Hypnotics, Sedatives
 cyclobarbital, pentobarbital, phenobarbital, methaqualone (BTM), benzodiazepines (flurazepam, midazolam, nitrazepam, lormetazepam, flunitrazepam, triazolam, brotizolam, temazepam, loprazolam)

Hypophysial and Hypothalamic Hormones, Regulatory Peptides and their Inhibitors
 corticotrophin, tetracosactide, choriogonadotropin, urofollitropin, urogonadotropin, somatropin, metergoline, bromocriptine, terlipressin, desmopressin, oxytocin, argipressin, ornipressin, leuprorelin, triptorelin, gonadorelin, buserelin, nafarelin, goselerin, somatostatin Immunotherapeutics and Cytokines
 dimepranol-4-acetatamidobenzoate, thymopentin, $\alpha$-interferon, $\hat{\alpha}$-interferon, $\gamma$-interferon, filgrastim, interleukins, azathioprine, cyclosporins Local Anaesthetics
 internal
  butanilicaine, mepivacaine, bupivacaine, etidocaine, lidocaine, articaine, prilocalne,
 externally, in addition
  propipocaine, oxybuprocaine, tetracaine, benzocaine Anti-Migraine Agents
 proxibarbal, lisuride, methysergide, dihydroergotamine, clonidine, ergotamine, pizotifen Narcotics
 methohexital, propofol, etomidate, ketamine, alfentanil, thiopental, droperidol, fentanyl Parathyroid Hormones, Calcium Metabolism Regulators
 dihydrotachysterol, calcitonin, clodronic acid, etidronic acid Opthalmics
 atropine, cyclodrine, cyclopentolate, homatropine, tropicamide, scopolamine, pholedrine, edoxudine, idouridine, tromantadine, aciclovir, acetazolamide, diclofenamide, carteolol, timolol, metipranolol, betaxolol, pindolol, befunolol, bupranolol, levobununol, carbachol, pilocarpine, clonidine, neostigmine Psychopharmacological Agents
 benzodiazepines (lorazepam, diazepam), clomethiazole, Thyroid Treatments
 1-thyroxine, carbimazole, thiamazole, propylthiouracil Sera, Immunoglobulins, Vaccines
 a) immunoglobulins generally and specifically such as hepatitis types, rubella, cytomegalia, rabies, FSME, varicella-zoster, tetanus, Rhesus factors
 b) immune sera such as botulism antitoxin, diphtheria, gas gangrene, snake venom, scorpion poison
 c) vaccines such as influenza, tuberculosis, cholera, diphtheria, hepatitis types, FSME, rubella, haemophilus influenzae, measles, neisseria, mumps, poliomyelitis, tetanus, rabies, typhus Sexual Hormones and their Inhibitors
 anabolics, androgens, antiandrogens, gestagens, oestrogens, antioestrogens (tamoxifen, etc.)

Cystostatics and Metastasis Inhibitors
 a) alkylating drugs such as nimustine, melphalan, carmustine, lomustine, cyclophosphamide, ifosfamide, trofosfamide, chlorambucil, busulfan, treosulfane, prednimustine, thiotepa,
 b) antimetabolites such as cytarabine, fluorouracil, methotrexate, mercaptopurine, tioguanine
 c) alkaloids such as vinblastine, vincristine, vindesine
 d) antibiotics such as aclarubicin, bleomycin, dactinomycin, daunorubicin, doxorubicin, epirubicin, idarubicin, mitomycin, plicamycin
 e) complexes of sub-group elements (e.g. Ti, Zr, V, Nb, Ta, Mo, W, Ru, Pt) such as carboplatin, cisplatin and metallocene compounds such as titanocene dichloride
 f) amsacrine, dacarbazine, estramustine, etoposide, hydroxycarbamide, mitoxanthrone, procarbazine, temiposide g) alkylamidophospholipids (described in J. M. Zeidler, F. Emling, W. Zimmermann and H. J. Roth, Archiv der Pharmazie, 324 1991, 687)

h) ether lipids such as hexadecylphosphocholine, ilmofosine and analogues, described in R. Zeisig, D. Arndt and H. Brachwitz, Pharmazie 45 (1990) 809-818)

i) taxanes such as e.g. paclitaxel

Peptide and protein active ingredients, in particular also recombinant peptides and proteins, such as e.g. cyclosporin, LH-RH analogues, follicle-stimulating hormone (FSH), gonadotropin-releasing hormone antagonist (GnRHA), human choriogonadotropin (hCG), growth hormone-releasing factor (GHRF), human growth hormone (hGH), interferon-beta la, human tumor-necrosis-factor-linking protein (HTBP), human interleukin-6 (HIL6), lymphocyte-activation gene 3, type 1 interferon receptor Active ingredients from the following chemical groups can generally be used.

hydroxylated hydrocarbons carbonyl compounds such as ketones (e.g. haloperidol), monosaccharides, disaccharides and amino sugars carboxylic acids such as aliphatic carboxylic acids, esters of aliphatic and aromatic carboxylic acids, basically substituted esters of aliphatic and aromatic carboxylic acids (e.g. atropine, scopolamine), lactones (e.g. erythromycin), amides and imides of aliphatic carboxylic acids, amino acids, aliphatic aminocarboxylic acids, peptides (e.g. cyclosporine), polypeptides, β-lactam derivatives, penicillins, cephalosporins, aromatic carboxylic acids (e.g. acetylsalicylic acid), amides of aromatic carboxylic acids, vinylogous carboxylic acids and vinylogous carboxylic acid esters carbon dioxide derivatives such as urethane and thiourethanes, urea and urea derivatives, guanidine derivatives, hydantoins, barbituric acid derivatives and thiobarbituric acid derivatives nitroso compounds such as aromatic nitroso compounds and heteroaromatic nitroso compounds amines such as aliphatic amines, aminoglycosides, phenylalkyl amines, ephedrine derivatives, hydroxyphenylethanolamines, adrenaline derivatives, amphetamine derivatives, aromatic amines and derivatives, quaternary ammonium compounds sulfurous compounds such as thiols and disulphanes sulphones, sulphonic acid esters and sulphonic acid amides polycarbocycles such as tetracyclines, steroids with aromatic ring A, steroids with an alpha, beta-unsaturated carbonyl function in ring A and alpha ketol group (or methylketo group) at C 17, steroids with a butenolide ring at C 17, steroids with a pentadienolide ring at C 17 and seco-steroids O-containing heterocycles such as chroman derivatives (e.g. cromoglycic acid)

N-containing heterocycles such as pyrazole derivatives (e.g. propyphenazone, phenylbutazone)

imidazole derivatives (e.g. histamine, pilocarpine), pyridine derivatives (e.g. pyridoxine, nicotinic acid), pyrimidine derivatives (e.g. trimethoprim), indole derivatives (e.g. indomethacin), lysergic acid derivatives (e.g. ergotamine), yohimbine derivatives, pyrrolidine derivatives, purine derivatives (e.g. allopurinol), xanthine derivatives, 8-hydroxyquinoline derivatives, amino-hydroxy-alkylated quinolines, aminoquinolines, isoquinoline derivatives (e.g. morphine, codeine), quinazoline derivatives, benzopyridazine derivatives, pteridine derivatives (e.g. methotrexate), 1,4-benzodiazepine derivatives, tricyclic N-containing heterocycles, acridine derivatives (e.g. ethacridine) and dibenzazepine derivatives (e.g. trimipramine) S-containing heterocycles such as thioxanthene derivatives (e.g. chlorprothixene)

N,O- and N,S-containing heterocycles such as monocyclic N,O-containing heterocycles, monocyclic N,S-containing heterocycles, thiadiazine derivatives, bicyclic N,S-containing heterocycles, benzothiadiazine derivatives, tricyclic N,S-containing heterocycles and phenothiazine derivatives O,P,N-containing heterocycles (e.g. cyclophosphamide).

Synthetic, semi-synthetic as well as natural polymers can be used. In particular can be considered e.g.

cellulose derivatives such as ethyl cellulose, methyl cellulose, hydroxyethyl cellulose, hydroxypropyl cellulose, sodium carboxymethylcellulose, methyl hydroxypropylcellulose, hydroxypropylmethylcellulose acetate succinate, carboxymethylcellulose, cellulose acetate phthalate, methyl hydroxyethylcellulose natural polymers such as alginates, albumin, in particular serum albumin, human albumin and bovine albumin, shellac, wax, beeswax, polishing waxes, collagen, casein, fibrin, bentonite, tragacanth, xanthans, polysaccharides such as chitin, dextrans, hyaluronic acid synthetic polymers such as polyacrylates, polymethacrylates, polyvinyl derivatives, polyester polymers such as polylactides, polyglycolides and their co-polymers, polyanhydrides, polyphosphoric esters, block polymers from polyethylene glycol and polyesters, polyhydroxybutyric acid, polycyanoacrylates, polycarbonates, polycaprolacton.

Active ingredients can also already be incorporated into the polymers before the homogenization, e.g. from the above-named therapeutic groups and/or chemical groups. The active ingredients can be e.g. dissolved, dispersed, solubilized or otherwise incorporated into the polymers.

The pre-suspension is then further processed, e.g. in one of the following dispersion systems: high-pressure homogenizers of the piston-gap homogenizer type (APV Gaulin Systeme, French press, Avestin), jet-stream homogenizers (e.g. Microfluidizer), rotor-stator systems (Ultra-Turrax, Silverson homogenizers), ultrasound bath, ultrasound rod and ultrasound homogenizers.

The prepared pre-suspension is homogenized at approx. 100 bar to approx. 2000 bar using one or more or many cycles. The pressures to be applied in the high-pressure homogenizer and the number of cycles are a function of the desired fineness of the particles. As a rule, the preparation of nanoparticles requires higher pressures (e.g. 1000 bar or more) and a greater number of cycles. The number of cycles likewise depends on the power density of the homogenizer (e.g. 4-20 cycles in the case of APV Gaulin machines, in some cases up to 50 or several hundred cycles in the case of the Microfluidizer).

The characterization of the superfine microparticle dispersions and nanoparticles was by means of laser diffractometry (LD) (Coulter LS230, Coulter Electronics, Miami, USA) and photon correlation spectroscopy (PCS) (Zetasizer 4, Malvern Instruments, Malvern, United Kingdom). Characterization parameters were the 50% (D50%), 90% (D90%) and 95% (D95%) LD diameter measured by LD. The PCS (measurement range approx. 3 nm-3 µm) gives the PCS diameter and, as a measure of the width of the distribution, the polydispersity index (PI) in the range from 0.000 (+ideal monodispersion) to 0.500 (very broad distribution), above 0.5 no further conclusions can be drawn with regard to the width of distribution.

The fineness of the prepared dispersion is based on the intended use. The target size for polymer particles often lies in the range of a few micrometers. Examples are dispersions of ethyl cellulose for coating tablets, or corticoid-loaded polylactide glycolide particles for internalisation by macrophages after intra-articular injection (target size approx. 1-2 µm). For poorly soluble drugs, the target size is often in the range of approx. 1 µm or in the nanometer range, e.g. azodicarbonamide. Through a suitable choice of pressure and cycle number, the target size can be controlled in the production process.

BRIEF DESCRIPTION OF THE DIAGRAMS

EXAMPLES

Example 1

The drug 1-[[2,7-bis(2,6-dimethyl-4-morpholinyl)-6-phenyl-4-pteridinyl]-(2-hydroxyethyl)-amino]-2-methyl-[cis[cis]]-propan-2-ol (1%) was dispersed in anhydrous glycerol with addition of Tween 80 (0.5%) and the obtained predispersion then high-pressure homogenized in a discontinuous Micron LAB40 (APV Deutschland GmbH, Lubeck, Germany). Production parameters were 2 cycles at 150 bar, then 2 cycles at 500 bar and then 6 cycles at 1500 bar. Homogenization was carried out at room temperature. Particle size analysis with the Coulter LS230 laser diffractometer (Coulter Electronics, USA). After the 6 cycles at 1500 bar, the D50% was 1.7 µm, the D90% 4.5 µm and the D95% 5.4 µm.

Example 2

To prepare nanoparticles, the drug from example 1 was homogenized as described there, but with 20 cycles at 1500 bar. The average PCS diameter determined by photon-correlation spectroscopy was 950 nm, the PI 0.513.

Example 3

The drug from example 1 (1%) was dispersed in anhydrous glycerol with addition of Tween 80 (0.5%) and a microparticle dispersion prepared as described in example 1, but homogenized with 10 cycles at 1500 bar. For comparison, the drug was also homogenized under identical conditions in purely aqueous dispersion (glycerol replaced by water). The diameters were 1.3 µm and 0.9 µm (D50%), and 3.2 µm and 2.3 µm (D90%) respectively.

Example 4

10% of the synthetic polymer Eudragit RS PO (polyacrylic acid trimethyl-aminoethylester, Röhm GmbH, Darmstadt, Germany) was dispersed in propylene glycol with addition of 1.5% Tween 80. The particle size determination of the powder dispersed with ultrasound showed a D50% of 79.7 µm and a D95% of 185 µm. Homogenization was carried out analogously to example 1 in the batch-operated Micron LAB40, production parameters were 2 cycles at 150 bar, 2 cycles at 500 bar and then 2 cycles at 1500 bar (room temperature). The PCS diameter of the nanoparticle dispersion was 123 nm, the polydispersity index 0.185. The D50% LD diameter of 139 nm and the D99% of 149 nm were thus in agreement.

Example 5

10% tragacanth was dispersed in Miglyol 812 with addition of 1% Span 80 and microparticles prepared as described in example 1. The average diameter determined by light microscopy was 7.54 µm after 10 cycles at 1500 bar.

Example 6

Two microparticle dispersions were prepared analogously to example 1, preparation parameters were 2 cycles at 150 bar, 2 cycles at 500 bar and 4 cycles at 1500 bar. One dispersion was anhydrous (0% water), the second contained 1.0% water. The diameters were 1.9 µm and 2.1 µm (D50%), and 4.9 µm and 5.4 µm (D90%) respectively.

Example 7

Two microparticle dispersions were prepared analogously to example 6. One dispersion contained 10% water, the second contained 30% water. The diameters were 1.7 µm and 1.7 µm (D50%), and 4.1 µm and 4.2 µm (D90%) respectively.

Example 8

A microparticle dispersion was prepared analogously to example 7 (4 cycles at 1500 bar), but with the water content increased to 50%. The D50% and D90% diameters remained unchanged, despite an increasing water content compared with example 7, at 1.5 µm and 3.7 µm respectively.

Example 9

Figure 1A:
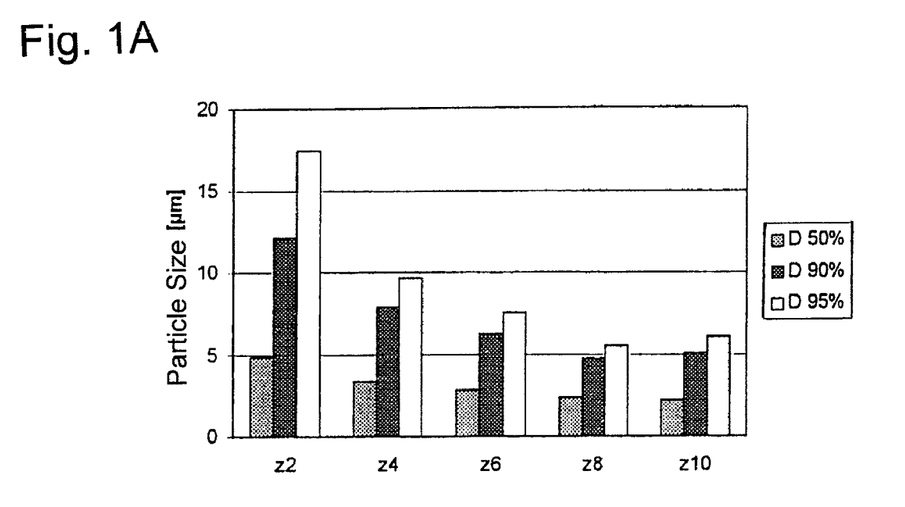
FIGS. 1A and 1B: 50%, 90% and 95% LD diameter of the microparticle dispersions from example 9 prepared with addition of plasticizer (top FIG. 1A) and the plasticizer-free dispersion according to the invention (bottom FIG. 1B) as a function of the number of homogenization cycles (2 to 10 cycles, 1500 bar).
Figure 1B:
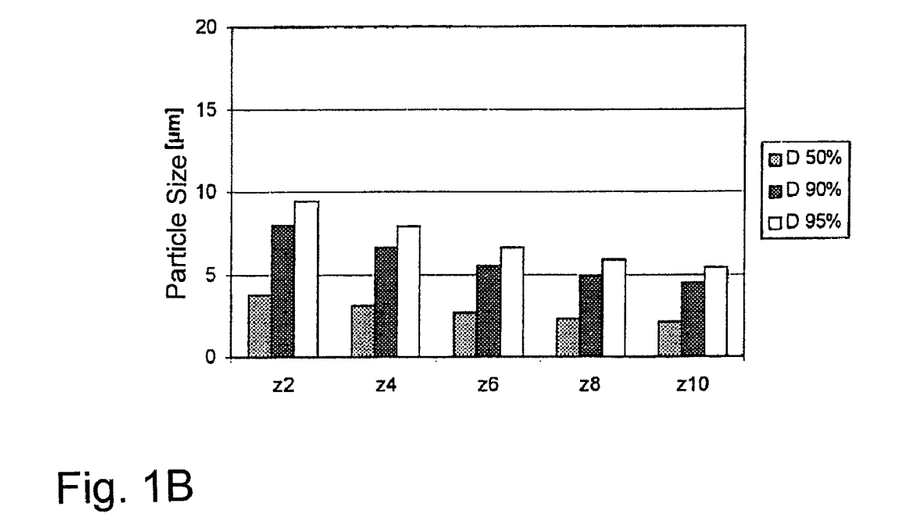

Determination of the influence of a plasticizer on the homogenization result: two ethyl cellulose (20 cP) dispersions were prepared by stirring. The composition of the plasticizer-free dispersion was: 10.0% ethyl cellulose, 1.18% oleic acid, 0.24% caustic soda and water to 100%. The plasticizer-containing dispersion additionally contained 1.74% dibutyl sebacate. Homogenization was carried out at 85° C., homogenization parameters were 2 cycles at 150 bar, 2 cycles at 500 bar and then varying numbers of cycles at 1500 bar. Five microparticle dispersions were prepared each with 2, 4, 6, 8 and 10 cycles at 1500 bar and the 50%, 90% and 95% diameters determined (diagram 1). The diameters of the plasticizer-free dispersion according to the invention are clearly lower, i.e. the addition of plasticizer does not promote the dispersability of the polymer.

Example 10

Figure 2:
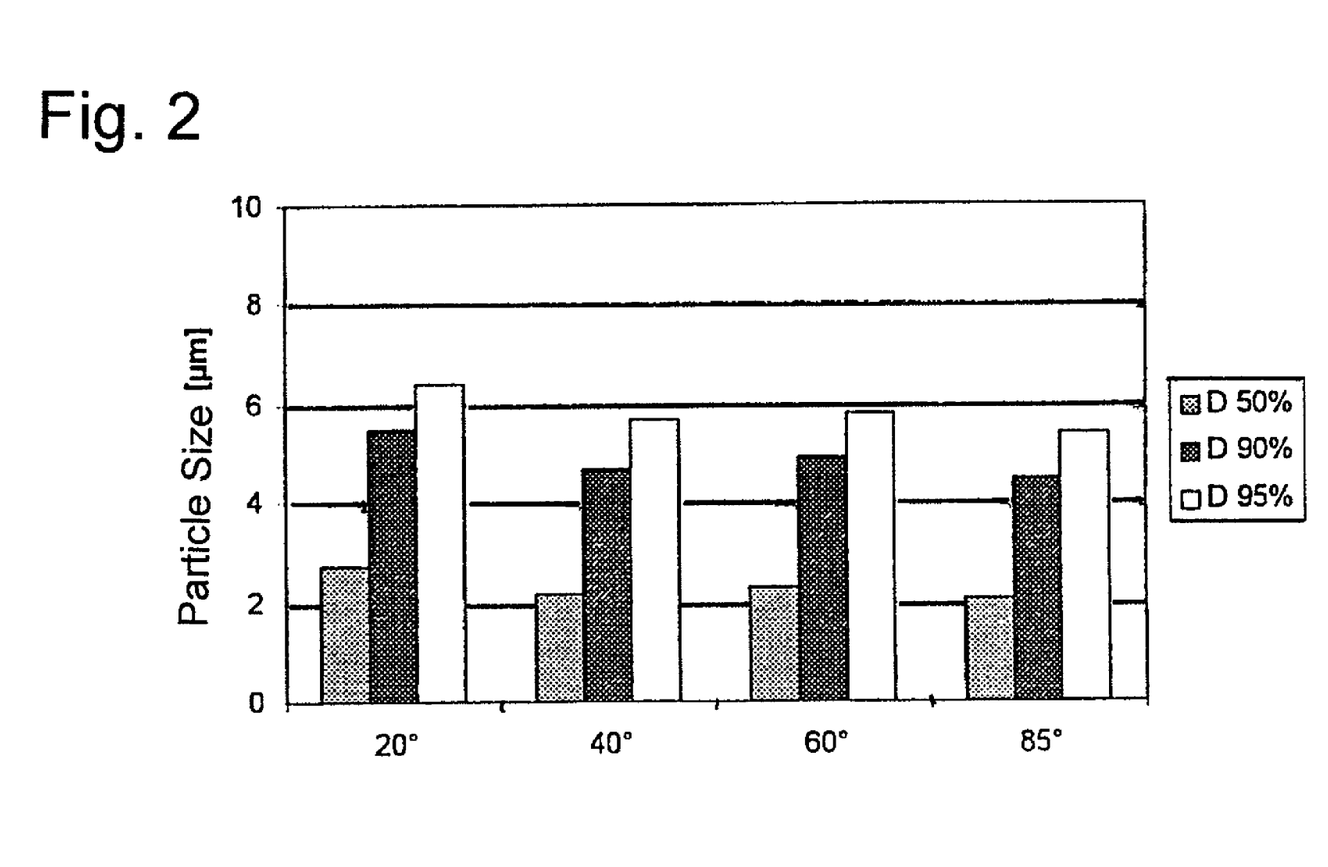
FIG. 2: 50%, 90% and 95% LD diameter of the plasticizer-free dispersion according to the invention from example 10 prepared at different temperatures (20°, 40°, 60° and 85° C.).

Determination of the influence of the temperature on the homogenization result: plasticizer-free ethyl cellulose dispersions were homogenized at different temperatures. The composition was identical to example 9, homogenization parameters were 2 cycles at 150 bar, 2 cycles at 500 bar and 10 cycles at 1500 bar, production temperatures of the four formulations were 20°, 40°, 60° and 85° C. The 50%, 90% and 95% diameters were determined by laser diffractometry (diagram 2) and do not change with the temperature.

Example 11

Figure 3A:
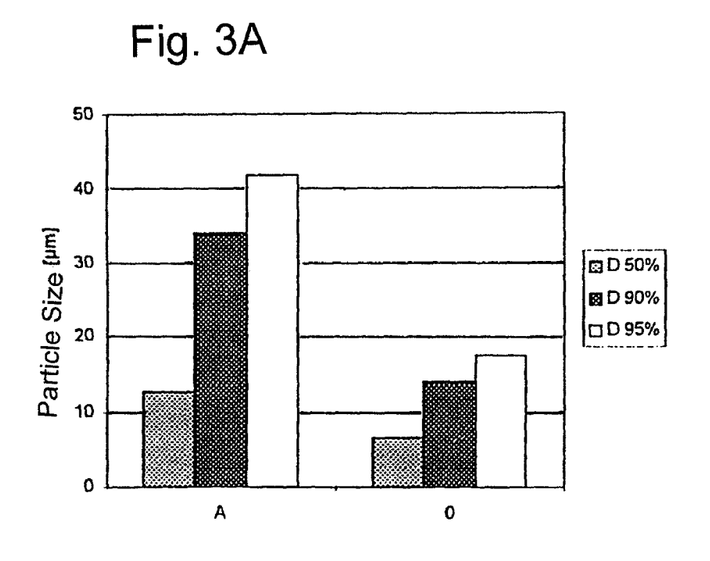
FIGS. 3A and 3B: 50%, 90% and 95% LD diameter of the microparticle dispersions from example 11 with added plasticizer (A) and the plasticizer-free dispersion according to the invention (0) prepared at 20° C. (left FIG. 3A) and at 40° C. (right FIG. 3B).
Figure 3B:
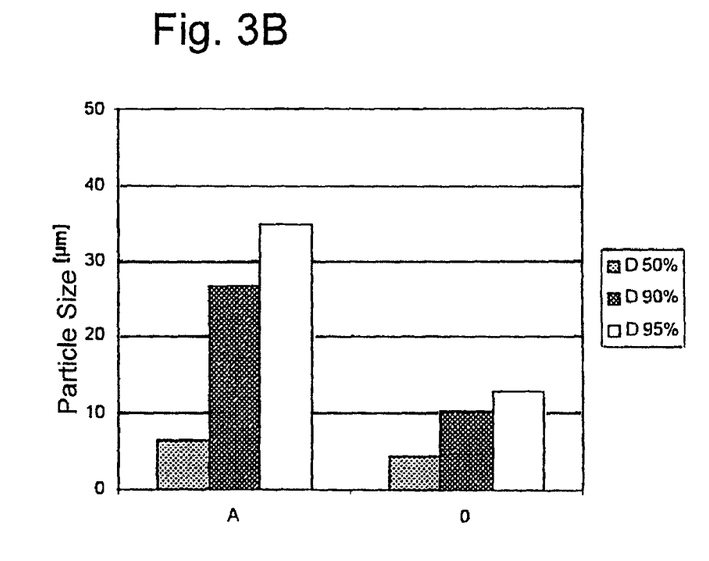
Figure 4:
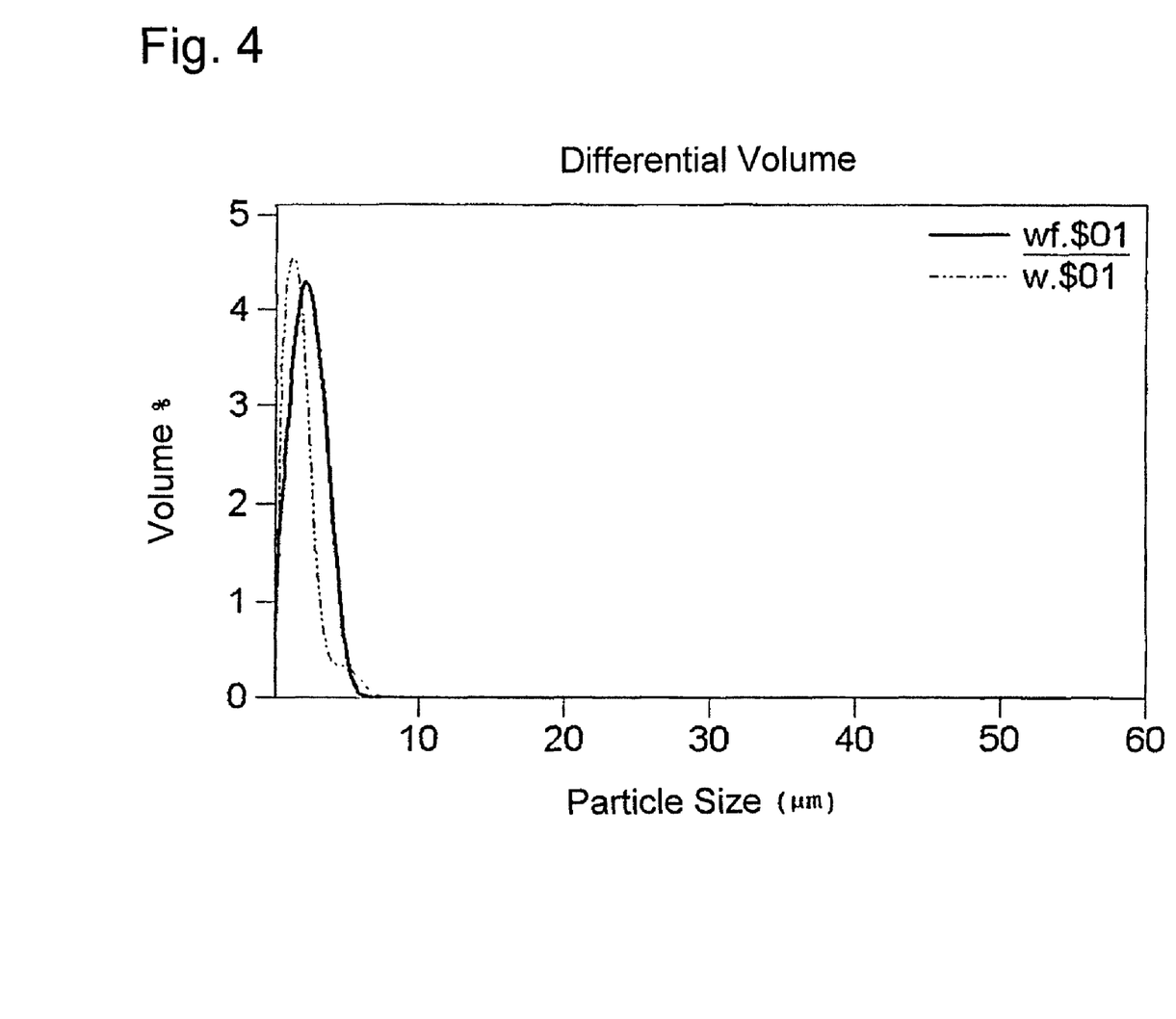
FIG. 4: Particle size distribution curves of the microparticle dispersion from example 3 prepared by homogenization in anhydrous (water-free) medium (WF) and for comparison in water (W).

Determination of the influence of a plasticizer on the homogenization result at lower temperature: two ethyl cellulose dispersions were prepared identically to example 9 (plasticizer-free dispersion, plasticizer-containing dispersion). The homogenization was carried out at 20° C. and 40° C. in each case, homogenization parameters were 2 cycles at 150 bar, 2 cycles at 500 bar and 2 cycles at 1500 bar. Diagram 3 shows the 50%, 90% and 95% diameters. The diameters of the plasticizer-free dispersion according to the invention are clearly lower, i.e. the addition of plasticizer hinders the dispersion process.

Example 12

The substance azodicarbonamide (ADA) (10%) was dispersed, with addition of Tween 80 (0.5%) in polyethylene glycol 400 (PEG 400) with stirring. The microparticle dispersion was prepared as described in example 1. Production parameters were 2 cycles at 150 bar, 2 cycles at 500 bar and then 4 cycles at 1500 bar. The 50% diameter was 3.0 µm, the D90% 6.2 µm and the D95% 7.2 µm.

Example 13

Reduction of the proportion of microparticles with a size clearly above the 50% diameter: the drug was dispersed analogously to examples 6 to 8 in dispersion media with 0% water (glycerol) 10%, 30%, 50% water (glycerol-water mixtures) and in 100% water (composition identical to examples 6-8). Homogenization was carried out as in examples 6-8, but with 10 cycles at 1500 bar. The D50% showed little change, the 95% diameter decreased from 3.9 µm (in 0% water, i.e. pure glycerol) to 2.8 µm in pure water (difference approx. 1.1 µm).

Alternatively, this effect can also be achieved in anhydrous media by simply increasing the number of homogenization cycles. In pure glycerol (0% water), the D95% decreases from 7.0 µm (after 2 cycles at 1500 bar) to 3.9 µm (after 10 cycles), i.e. difference approx. 3.1 µm.

Example 14

Preparation of a Clinical Batch Under Oxygen-Poor Conditions and protective gassing: azodicarbonamide (1) was dispersed with addition of Tween 80 (0.2%) analogously to example 12 in 2 kg propylene glycol and homogenized (homogenization pressure: 700 bar, room temperature) in a cyclical process for 30 minutes with a Micron LAB 60 (APV Deutschland GmbH, Lubeck, Germany). Propylene glycol was degassed beforehand by heating. The product container was kept under nitrogen. The average diameter determined by light microscopy was 5.45 µm after 30 minutes' homogenization time.

Example 15

1% cyclosporin was dispersed, with addition of 1% Tween 80, in propylene glycol with stirring with an Ultra-Turrax (9500 rpm, 1 minute) and then homogenized in LAB 40 at room temperature for cycles at 150 bar. The PCS diameter was 203 nm, the polydispersity index 0.132. An increase of the cyclosporin proportion to 5% resulted in particles with 182 nm, PI 0.131. The particles are to be separated after preparation, e.g. by centrifuging.

Example 16

1% PLA/GA (Resomer RG 504, Boehringer Ingelheim, Germany) was dispersed, with addition of 0.5% Tween 80 in propylene glycol with stirring and then homogenized in Micron LAB 40 for 2 cycles at 100 bar and 8 cycles at 150 bar. The 50% LD diameter was 19.0 µm.

Example 17

1% medical-grade charcoal was milled with polypropylene glycol, with addition of 1% Tween 80, then dispersed with an Ultra-Turrax (9500 rpm, 1 minute) and then homogenized below room temperature at 4° C. in a LAB 40. Production parameters were 2 cycles at 150 bar, 2 cycles at 500 bar and 5 cycles at 1500 bar. The 50% diameter was 5.6 µm, the D90% 13.5 µm and the D95% 16.1 µm. A second batch of identical composition was homogenized at −20° C. The 50% diameter was 5.5 µm, the D90% 13.0 µm and the D95% 15.3 µm.

The invention claimed is:

1. Process for the gentle preparation of superfine micro- and nanoparticles having a particle size, as average diameter of the number distribution, of 5.6 µm or less, the method comprising:
    subjecting a matrix material comprising solid particles to a high-pressure homogenizing process in a piston-gap homogenizer in an anhydrous or water-reduced dispersion medium containing less than 50 wt. % of water in which the solid particles are suspended and at temperatures of 20° C. or less, which leads to a gentle particle size reduction with minimization of the impairment of the chemical stability of the homogenized material, to form superfine micro- and nanoparticles.

2. Process according to claim 1, wherein the homogenized matrix material comprises at least one selected from the group consisting of drugs, pharmaceutical active ingredients, veterinary drugs, active ingredients, auxiliaries, additives for cosmetics, agricultural products, foodstuffs and preservatives.

3. Process according to claim 2, wherein the homogenized matrix material comprises at least one drug selected from the group consisting of ciclosporin, azodicarbonamide, paclitaxel, prednisolone, carbamazepine, taxol, morphine, diclofenac, ibuprofen, phenobarbital and cromoglycin.

4. Process according to claim 1, wherein the homogenized matrix material comprises at least one selected from the group consisting of synthetic, semi-synthetic or natural polymers, and natural macromolecules.

5. Process according to claim 4, wherein the homogenized matrix material comprises at least one selected from the group consisting of synthetic polymers, polylactide, polyglycolide, polylactide/-glycolide co-polymer, polyorthoester, polyhydroxybutyrate (PHB), polyhydroxyvaleriate (PHV), polyhydroxybutyrate/-valeriate co-polymer, polyacrylates, polymethacrylates, polyvinyl derivatives, block polymers of polyethylene glycol and polyesters, polyhydroxybutyric acid, polycyanoacrylates, polycarbonates and polycaprolacton.

6. Process according to claim 4, wherein the homogenized matrix material comprises at least one selected from the group consisting of natural macromolecules, alginates, albumin, serum albumin, human albumin, bovine albumin, collagen, casein, fibrin, tragacanth, xanthans, polysaccharides, chitin, dextrans and hyaluronic acid.

7. Process according to claim 1, wherein the homogenized matrix material comprises polymers or natural macromolecules loaded with drugs or active ingredients.

8. Process according to claim 7, wherein the homogenized matrix material comprises at least one polymer selected from the group consisting of polylactide, polyglycolide, polylactide/-glycolide co-polymer, polyorthoester, polyhydroxybutyrate (PHB), polyhydroxyvaleriate (PHV), and polyhydroxybutyrate/-valeriate co-polymer.

9. Process according to claim 7, wherein the homogenized matrix material comprises at least one selected from the group consisting of natural macromolecules, in particular alginates, albumin, preferably serum albumin, human albumin and bovine albumin, collagen, casein, fibrin, bentonite, tragacanth, xanthans, polysaccharides such as chitin, dextrans and hyaluronic acid.

10. Process according to claim 1, wherein the materials to be reduced in size are dispersed in a non-aqueous dispersion medium.

11. Process according to claim 10, wherein the materials to be reduced are dispersed in an oily medium.

12. Process according to claim 10, wherein the materials to be reduced are dispersed in liquid hydrocarbons.

13. Process according to claim 10, wherein the materials to be reduced are dispersed in at least one selected from the group consisting of polyethylene glycols (PEGs), PEG 100 to PEG 1000, anhydrous glycerol, anhydrous alcohols, methanol, ethanol, 1-propanol, isopropanol, n-butanol, 2-butanol, pentanol, hexanol, octanol, decanol, allyl alcohol, propargyl alcohol, ethanol, isopropanol butanol, and propylene glycols.

14. Process according to claim 10, characterized in that the materials to be reduced are dispersed in dimethyl sulfoxide.

15. Process according to claim 1, wherein the materials to be reduced are dispersed in a dispersion medium that contains a small or minimized proportion or proportion desired, for product-related reasons, of water.

16. Process according to claim 15, wherein the materials to be reduced are dispersed in a dispersion medium containing less than 5 wt. % water.

17. Process according to claim 15, wherein the materials to be reduced are dispersed in a dispersion medium which contains less than 10 wt. % water.

18. Process according to claim 15, wherein the materials to be reduced are dispersed in a dispersion medium comprising water and at least one dissolved substance selected from the group consisting of polymers, polyethylene glycols solid at room temperature, PEG 6000, cellulose derivatives, and hydroxypropyl methylcellulose (HPMC).

19. Process according to claim 1, wherein the process temperature is below the freezing point of water.

20. Process according to claim 1, wherein the process is carried out with the exclusion of oxygen.

21. Process according to claim 1, further comprising degassing the dispersion medium before use.

22. Process according to claim 1, wherein the particle size is less than 5 µm.

23. Process according to claim 1, wherein the particle size is less than 1 µm.

24. Process according to claim 1, wherein the homogenization process is conducted at temperatures below the freezing point of water.

25. Process according to claim 11, wherein the oily medium comprises at least one selected from the group consisting of medium chain triglycerides (MCT), peanut oil, avocado oil, cottonseed oil, safflower oil, long chain triglycerides (LCT), in particular soybean oil, triacetin and isopropyl myristate.

26. Process according to claim 12, wherein the liquid hydrocarbon comprises at least one selected from the group consisting of fluid paraffin, viscous paraffin, hexane and octane.

27. Process according to claim 16, wherein the dispersion medium contains less than 1 wt. % of water.

28. Process according to claim 1, wherein the process temperature is 4° C.

29. Process according to claim 19, wherein the process temperature is below −20° C.

30. Process according to claim 19, wherein the process temperature is below −50° C.

31. Process according to claim 20, further comprising gassing the matrix material and medium with inert gases.

32. Process according to claim 31, wherein the inert gas comprises at least one selected from the group consisting of nitrogen and argon.

33. Process according to claim 20, wherein the homogenization process is conducted under a vacuum.

34. Process according to claim 1, wherein the homogenizing process is conducted in a piston-gap homogenizer in an anhydrous medium.

35. Process for the gentle preparation of superfine micro- and nanoparticles having a particle size, as average diameter of the number distribution, of 5.6 µm or less, the method comprising:
dispersing solid particles in an anhydrous or water-reduced dispersion medium containing less than 50 wt. % of water to form a pre-suspension; and
subjecting the pre-suspension to a high-pressure homogenizing process in a piston-gap homogenizer to reduce the particle size without cavitation with minimization of the impairment of the chemical stability of the homogenized material, to form superfine micro- and nanoparticles.

36. Process for the gentle preparation of superfine micro- and nanoparticles having a particle size, as average diameter of the number distribution, of 5.6 µm or less, the method comprising:
dispersing solid particles comprising a drug, pharmaceutical active ingredient, or veterinary drug in an anhydrous or water-reduced dispersion medium containing less than 50 wt. % of water to form a pre-suspension; and
subjecting the pre-suspension to a high-pressure homogenizing process in a piston-gap homogenizer to reduce the particle size without cavitation with minimization of the impairment of the chemical stability of the homogenized material, to form superfine micro- and nanoparticles comprising the drug, pharmaceutical active ingredient, or veterinary drug.

* * * * *